MINIATURE ROSE PLANT
Filed Nov. 5, 1975
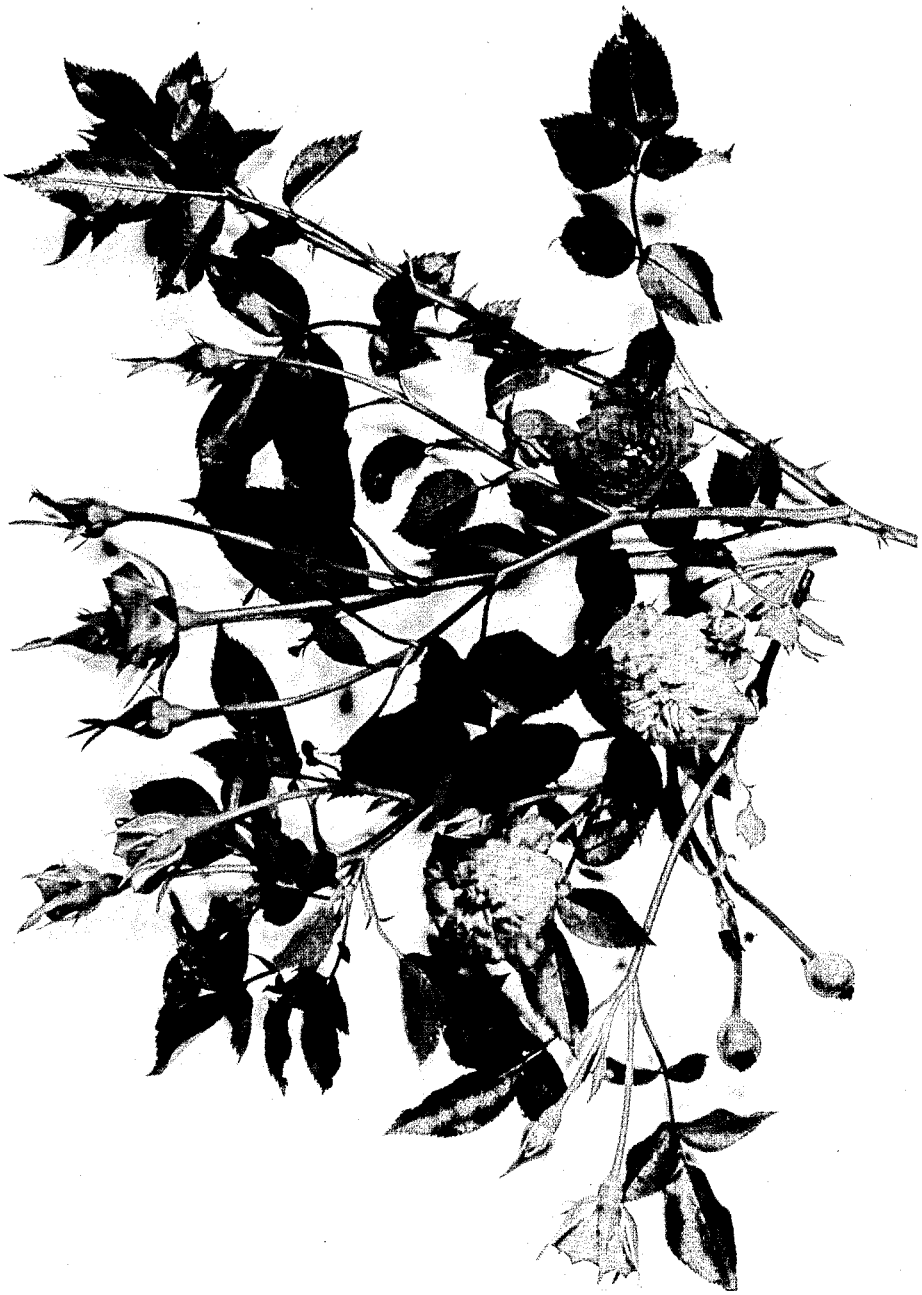

United States Patent

Plant Pat. 3,963

Patented Oct. 19, 1976

3,963

MINIATURE ROSE PLANT

Ralph S. Moore, 2519 E. Noble Ave.,
Visalia, Calif. 93277

Filed Nov. 5, 1975, Ser. No. 629,037

Int. Cl.[2] A01H 5/00

U.S. Cl. Plt.—10 1 Claim

The present invention relates to a new and distinct variety of hardy, dwarf, bush type rose plant of the miniature class; the variety being primarily characterized—as to novelty—by buds and flowers resembling Top Secret (miniature—not patented) in general form and by medium red buds and flowers which in general color effect are light to medium red when grown outdoors (light to medium red with an orange red cast when grown in plastic greenhouse).

The variety is further characterized by:

An abundance of bloom, with flowers usually borne several to stem in loose cluster or spray.

Moderate fragrance.

A plant which is quite vigorous, of rounded upright shape, and with glossy, medium foliage with pointed leaflets; the flowers and foliage being similar in size to the variety Top Secret (miniature—not patented). The plant, which has a normal average height of 12 to 16 inches at maturity, can be easily maintained at lesser height by occasional trimming.

A plant which grows and blooms satisfactorily both in greenhouse and outdoors; is a good plant for growing in pots; and provides excellent garden decoration as well as cut flowers.

The present variety of miniature rose was originated by me at my nursery located at Visalia, Calif., under conditions of careful control and observation, as a cross between an un-named red seedling Floribunda (not patented) as the seed parent and an un-named miniature rose (Little Darling × Red germain) as the pollent parent.

Subsequent to origination of the variety I successfully asexually reproduced it in my nursery located as aforesaid, by budding as well as by cuttings; the reproductions having run true in all respects.

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: hardy; dwarf; bush; seedling; greenhouse; outdoors; cut flowers; garden decoration potted plant.

Class: Miniature.

Flowers:

*Continuity.*—Continuous repeat bloom all season.

*Fragrance.*—Little to moderate.

Flowers borne: Usually several together (3 to 5 ro more) on normal strength medium length stems.

Quantity of bloom: Abundant both outside and in greenhouse.

Bud:

*Peduncle.*—Medium length slender; erect; medium green often tinted bronze (outdoors); very small short stiff hairs and sometimes some short prickles. Before calyx breaks, size—small. Form medium long; pointed with foliaceous appendages and numerous tiny short hairs on surface of the bud; with foliaceous parts extending beyond the tip of the bud equal to one-half or more of its length.

*Color.*—Medium green, usually tinted bronze (outdoors). As calyx breaks, color—red. As first petal opens: red, showing near-white at base of petal; size—small. Form; medium length; pointed; becoming rounded or high centered. Opening—opens well in all weather.

Bloom:

*Size when fully open.*—Small, averaging 35–38 mm. (up to 1½"). Petalage—varies with culture and season—double (20 petals) to 40 or more (plus several narrow petaloids) arranged regularly.

*Form.*—Slightly cupped at first, with petals rolled loosely outward, and later at maturity becoming high centered with petals being loosely rolled outward.

Petals: Thick; satiny both inside and outside. Shape—outside petals oval (broad lanceolate with acute tips); intermediate—broad lanceolate with acute tip; inside narrow lanceolate.

Color: Newly opened flower from a plant grown in plastic house (October 1975), Visalia, Calif.

*Outside petal.*—Outside surface—near Currant Red 821 overlaid with darker red with large white area at base; inside surface—near Geranium Lake 20 overlaid with darker areas on upper ⅓ of petal shading to near white at base.

*Intermediate petal.*—Outside surface—near Currant Red 821 with white area at base then extending in somewhat irregular narrow area or band to tip of petal; inside—near Geranium Lake 20 overlaid with darker red on upper ½ of petal with small near white area at base.

*Inner petal.*—Outside surface—essentially same as intermediate petal; inside surface—similar to intermediate petal.

*General color effect newly opened flower.*—Bright medium red. Three days open—medium red. Behavior—spent petals may remain for time then drop off. Flower color is quite lasting even in warm weather. Flower longevity (June 1975)—both in garden or pot—5–7 days. Cut Flowers at living room temperature 3 to 5 days.

Reproductive organs:

*Stamens.*—Fairly abundant on less double flowers; few or none on more double flowers.

*Filaments.*—Medium length; white.

*Pollen.*—Fairly abundant.

*Pistils.*—Moderate number.

*Styles.*—Fairly even; medium length; bunched; well formed.

*Ovaries.*—All enclosed in calyx.

*Hips.*—Several.

*Sepals.*—Permanent; spear shaped (usually remain in contact with petals, instead of turning down, on opening or freshly opened flowers).

*Seeds.*—Several.

Foliage:

*Leaves.*—Compound of five leaflets (sometimes 7); abundant; small to moderately small; leathery; semi-glossy.

*Leaflets.*—Shape: Lanceolate; apex acute; base rounded or rounded acute. Margin serrate. Color: normal green; new growth often tinted bronze. Rachis: medium strength; upper side slightly hairy, grooved, underside sparsely thorny. Stipules: medium length; narrow; short to medium length points, turning out at an angle of 45 degrees or more.

Growth:

*Habit.*—Dwarf; bushy; upright; much branched.

*Growth.*—Free; vigorous.

*Canes.*—Medium; slender.

*Main stems.*—Color: dull green. Thorns: moderately thorny; medium length; hooked slightly downward. Color—medium gray brown. Prickles—none. Hairs—none. Branches—color: medium green. Thorns: moderately thorny; short; hooked slightly downward; medium length oval base. Prickles: none. Hairs—none. New Shoots—Color: medium green, often tinted bronze. Thorns: moderately thorny; medium length; hooked slightly downward; sharp points; base oval. Prickles: Few to none.

The miniature rose plant and its flowers as herein described may vary in slight detail due to climatic, soil and cultural conditions under which the variety may be grown; the present description being of the variety as grown at Visalia, Calif.

The following is claimed:

1. A new and distinct variety of miniature rose plant of hardy, dwarf, upright, much branched, bush type as illustrated and described, characterized by buds and flowers resembling the Top Secret (not patented) miniature rose in general form but color is lighter red with darker shading and a slight orangish cast, the general color effect being medium red; and further characterized by a plant which is of vigorous and compact growth, easy to propagate from cuttings with medium small glossy foliage and an abundance of bloom, with flowers borne usually several to stem in loose cluster or spray.

No references cited.

ROBERT E. BAGWILL, Primary Examiner